(12) United States Patent
Allemann et al.

(10) Patent No.: US 7,484,736 B2
(45) Date of Patent: Feb. 3, 2009

(54) ACCESSORY FOR A ROTARY TOOL

(75) Inventors: Markus Allemann, Grayslake, IL (US); Edward G. Ennis, Niles, IL (US); Vera Maras, Schaumburg, IL (US); Jose Nieto, Chicago, IL (US)

(73) Assignee: Robert Bosch GmbH, Stuttgart (DE)

( * ) Notice: Subject to any disclaimer, the term of this patent is extended or adjusted under 35 U.S.C. 154(b) by 349 days.

(21) Appl. No.: 11/187,140

(22) Filed: Jul. 21, 2005

(65) Prior Publication Data
US 2007/0018413 A1 Jan. 25, 2007

(51) Int. Cl.
*B24B 41/00* (2006.01)

(52) U.S. Cl. .......................... 279/143; 279/93; 451/342

(58) Field of Classification Search ................. 279/93, 279/94, 102, 133, 134, 143; 451/342
See application file for complete search history.

(56) References Cited

U.S. PATENT DOCUMENTS

| | | | |
|---|---|---|---|
| 480,121 A | 8/1892 | Nichols | |
| 505,121 A | 9/1893 | Nelson | |
| 514,882 A * | 2/1894 | Elliott | 433/134 |
| 583,472 A | 6/1897 | Heath, Jr. | |
| 769,426 A | 9/1904 | Zeran | |
| 1,125,153 A * | 1/1915 | Nielson | 15/179 |
| 1,333,054 A | 3/1920 | Abbott | |
| 1,355,888 A * | 10/1920 | Burlew | 51/299 |
| 1,941,840 A | 1/1934 | Kelsey | |
| 2,276,067 A | 3/1942 | Siqveland | |
| 2,839,879 A * | 6/1958 | Eisenbeis | 451/509 |
| 3,239,971 A * | 3/1966 | Freerks et al. | 451/511 |
| 3,574,978 A * | 4/1971 | Block | 451/509 |
| 3,667,169 A * | 6/1972 | MacKay, Jr. | 451/511 |
| 4,015,371 A * | 4/1977 | Grayston | 451/342 |
| 4,245,438 A * | 1/1981 | van Buren, Jr. | 451/509 |
| 4,601,661 A * | 7/1986 | Du Be et al. | 433/134 |
| 4,624,876 A * | 11/1986 | Nevin | 428/66.6 |
| 4,657,428 A * | 4/1987 | Wiley | 403/359.3 |
| 4,683,683 A * | 8/1987 | Block | 451/509 |
| 4,730,952 A * | 3/1988 | Wiley | 403/316 |
| 4,889,489 A | 12/1989 | Von Weissenfluh | |
| 4,988,294 A * | 1/1991 | DuBe et al. | 433/134 |
| D394,530 S * | 5/1998 | Roeker | D32/25 |
| 6,701,629 B2 * | 3/2004 | Krondorfer et al. | 30/390 |
| 6,743,085 B2 * | 6/2004 | Fritz et al. | 451/308 |

FOREIGN PATENT DOCUMENTS

| | | |
|---|---|---|
| EP | 0 832 614 | 4/1998 |
| WO | WO 98/43779 | 10/1998 |

* cited by examiner

*Primary Examiner*—David P Bryant
*Assistant Examiner*—Eric A Gates
(74) *Attorney, Agent, or Firm*—Maginot, Moore & Beck

(57) ABSTRACT

A rotary tool accessory includes a body defining an axis of rotation and having a work piece contacting surface and a drive portion. The body has defined therein a body opening including a first opening portion and a second opening portion. The rotary tool accessory further includes an insert located within at least the second body opening. The first opening portion is contained within a space during rotation of the body about the axis. Both the drive portion and the second opening portion are advanced through a path during rotation of the body about the axis, the path being located outside of the space.

18 Claims, 11 Drawing Sheets

ACCESSORY FOR A ROTARY TOOL

BACKGROUND

This invention relates to the field of hand held rotary tools and related accessories.

Hand held rotary tools are widely used by many people, including craftspeople, homeowners, and artists. These rotary tools typically include an outer housing designed to be easily held within a human hand. The housing retains an electric motor which is operable to drive a rotatable chuck of the rotary tool. A mandrel may be releasably coupled to the chuck so as to be rotatably driven by the rotary tool. In turn, an accessory may be releasably secured to the mandrel thereby enabling the rotary tool to rotatably drive the accessory. The accessory may be a cut-off wheel, a polishing wheel, a grinding wheel, a sanding disc, or any other similar member.

There exists a variety of mandrels that are configured to releasably secure an accessory thereto. One such mandrel includes a base having a threaded aperture and a clamping screw that cooperate to clamp the accessory to the mandrel between the base and the clamping screw. With the accessory so clamped, rotation of the mandrel by the rotary tool causes rotation of the accessory thereby allowing the user to perform work on a workpiece.

In order to change an accessory that is secured to a mandrel of the type described above, it is typically necessary to loosen the clamping screw from the base. Of course, in order to loosen the clamping screw, the user must first obtain an appropriately sized screwdriver, which may not be immediately available to the user. Furthermore, some users find the task of turning a screw tedious. Also, once the clamping screw is separated from meshing engagement from the base, the clamping screw is susceptible to being inadvertently dropped and lost since it is a relatively small, separate component. Accordingly, it would be advantageous to provide a mandrel and associated accessory that is quick and easy to use and does not require the use of an additional tool such as a screwdriver, or the use of a relatively small, separate component such as a clamping screw.

SUMMARY

In accordance with one embodiment of the present invention, there is provided a rotary tool accessory includes a body defining an axis of rotation and having a work piece contacting surface and a drive portion. The body has defined therein a body opening including a first opening portion and a second opening portion. The rotary tool accessory further includes an insert located within at least the second body opening. The first opening portion is contained within a space during rotation of the body about the axis. Both the drive portion and the second opening portion are advanced through a path during rotation of the body about the axis, the path being located outside of the space.

Pursuant to another embodiment, there is provided a rotary tool accessory that includes a rotary tool accessory that includes a body defining an axis of rotation and having a work piece contacting surface and a drive portion, the body having defined therein a body opening positioned adjacent to the drive portion. The rotary tool accessory also includes an insert attached to the body. The body opening includes a first opening portion and a second opening portion. The first opening portion is contained within a space defined by a circle during rotation of the body about the axis. The drive portion is advanced through a path during rotation of the body about the axis, the path being located outside of the circle. The second opening portion is advanced through the path during rotation of the body about the axis. Also, the at least part of the insert is positioned within the second opening portion.

In accordance with yet another embodiment, there is provided a rotary tool accessory that includes a body having (i) an outer wall structure defining a circular outer periphery, (ii) an inner wall structure defining a body opening, and (iii) a drive portion that defines a portion of the inner wall structure. The accessory tool further includes an insert located within the body opening. The body opening includes a first opening portion and a second opening portion. The first opening portion is contained within a space during rotation of the body about the axis. The drive portion is advanced through a path during rotation of the body about the axis, the path being located outside of the space. The second opening portion is advanced through at least part of the path during rotation of the body about the axis. In addition, the at least part of the insert is positioned within the second opening portion.

DESCRIPTION

Figure 1:
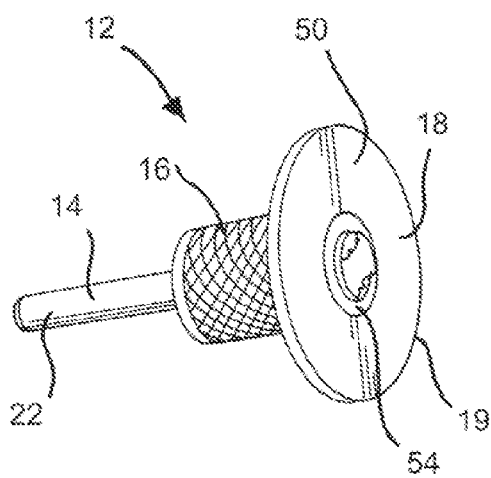
FIG. 1 shows a front perspective view of a mandrel assembly for use with a rotary tool having an accessory attached thereto.
Figure 2:
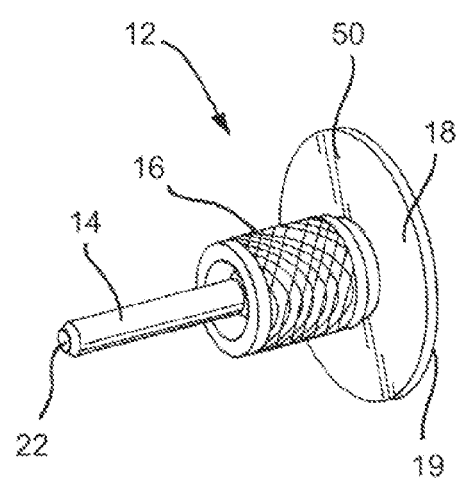
FIG. 2 shows a rear perspective view of the mandrel assembly and accessory of FIG. 1.
Figure 3:
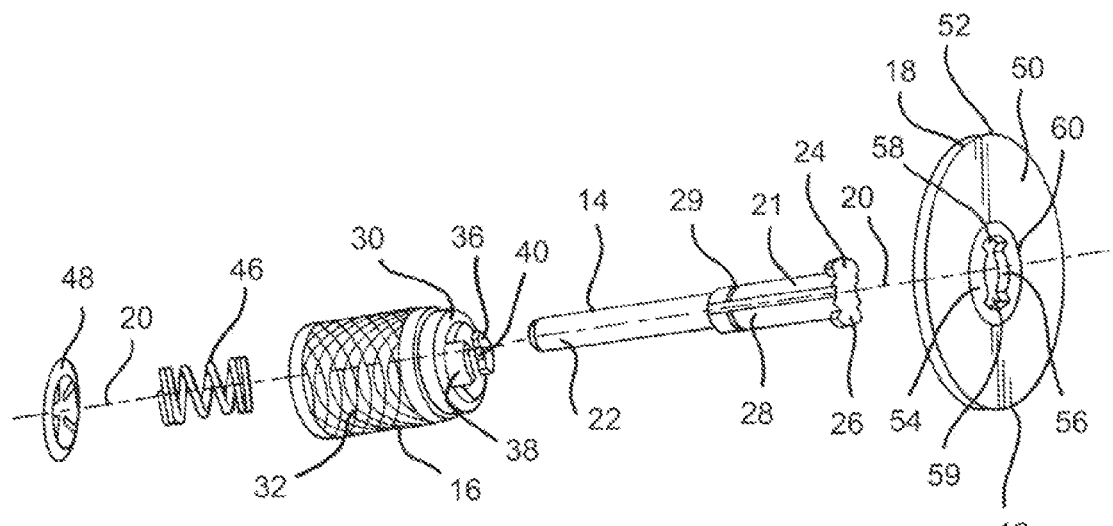
FIG. 3 shows an exploded perspective view of the mandrel assembly and accessory of FIG. 1.

A mandrel assembly for use with a rotary tool is shown in FIGS. 1-3. The mandrel assembly 12 includes a mandrel shaft 14 and a collar 16 slideable along the mandrel shaft. An accessory 18 in the form of a cut-off wheel 19 is configured to be releasably attached to the mandrel assembly. The mandrel shaft 14 of the mandrel assembly 12 is designed to be releasably coupled to a chuck of a rotary tool which includes an electric motor (not shown). Operation of the rotary tool rotates the chuck which in turn rotates the mandrel shaft 14 thereby imparting rotary movement to the cut-off wheel 19.

Figure 7:
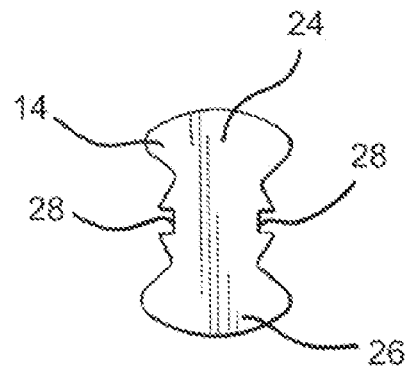
FIG. 7 shows a top elevational view of a shaft of the mandrel assembly of FIG. 5.
Figure 8:
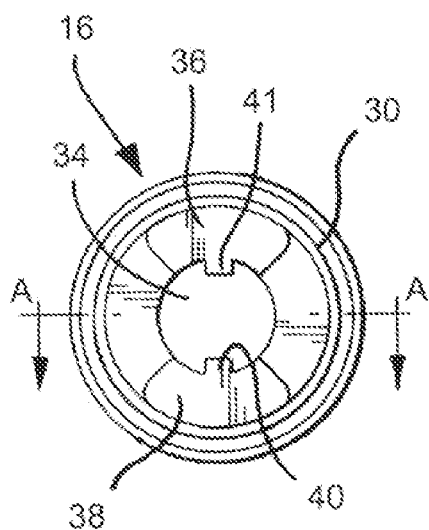
FIG. 8 shows a front elevational view of a collar of the mandrel assembly of FIG. 5.

The mandrel shaft 14 is comprised of a rigid material, such as steel. The mandrel shaft 14 defines a mandrel axis 20 and includes a first end portion 21 and a second end portion 22. The first end portion 21 of the mandrel shaft 14 comprises two opposing shaft teeth 24 and 26 extending from the end of the shaft 14 perpendicular to the mandrel axis 20. The shaft teeth 24 and 26 are generally arc or fan shaped when viewed individually. When viewed together, the shaft teeth 24 and 26 form a bow tie shape, as is seen in FIG. 3. (See also FIG. 7.)

Elongated grooves 28 are formed on opposite sides of the first end portion 21 of the mandrel shaft 14. The opposing elongated grooves 28 are parallel to the mandrel axis 20. A circular groove 29 extends circumferentially about the mandrel axis 20 and intersects the elongated grooves 28. The second end portion 22 of the mandrel shaft 14 is generally cylindrical in shape and is configured to be received within a chuck of a rotary tool.

With continued reference to the embodiment shown in FIGS. 1-3, the collar 16 is also comprised of a rigid material such as steel. The collar 16 is cylindrical in shape and forms a sleeve that surrounds a portion of the mandrel shaft 14. The collar 16 includes a head portion 30 with a skirt 32 depending from the head portion 30. As best seen in the embodiment shown in FIG. 9, the head portion 30 includes a circular head wall 31 positioned perpendicular to the skirt 32. An opening 34 is provided through the head portion 30, including the circular wall 31. The collar of FIGS. 5-6 and 8-9 is similar to the collar of FIGS. 1-3, with a few exceptions, as discussed in further detail below. However, in both embodiments, the opening 34 is designed and dimensioned to receive the mandrel shaft 14.

As shown in the embodiments of FIGS. 1-3 and FIGS. 5, 6, 8, 9, two opposing collar teeth 36 and 38 extend from the head 30 about the opening 34, but do not block the opening 34. The collar teeth 36 and 38 are each individually arc or fan shaped and together form two flared portions of a bow tie shape. The collar teeth 36 and 38 include tangs 40 and 41. Each tang 40 or 41 extends toward the opposing collar tooth 38 or 36. The tangs 40 and 41 are configured to be received within the elongated grooves 28 of the mandrel shaft 14.

Figure 9:
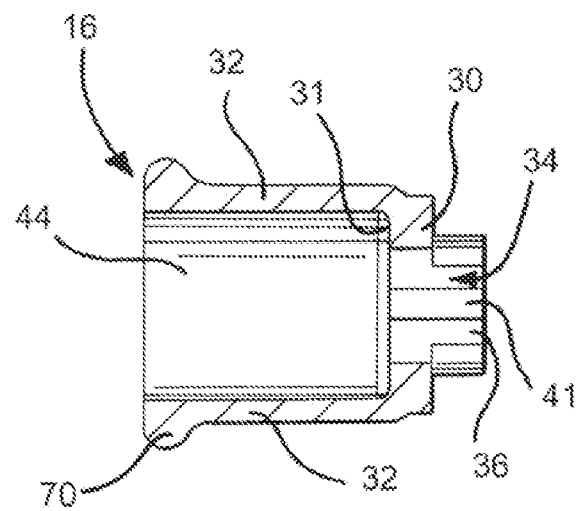
FIG. 9 shows a cross-sectional view of the collar along line A-A of FIG. 8.
Figure 10:
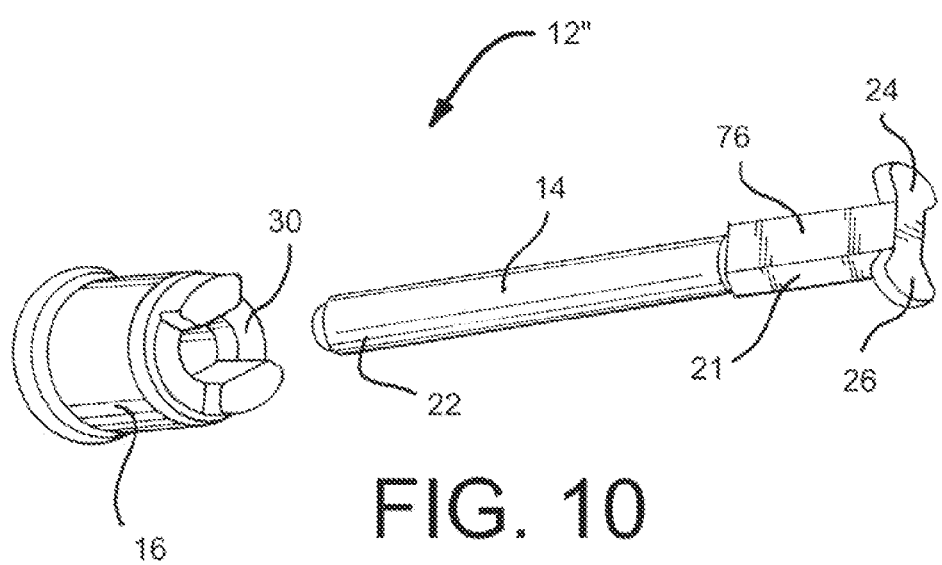
FIG. 10 shows another alternative embodiment of a mandrel assembly for use with a rotary tool with various components of the mandrel assembly omitted for ease of understanding.
Figure 11:
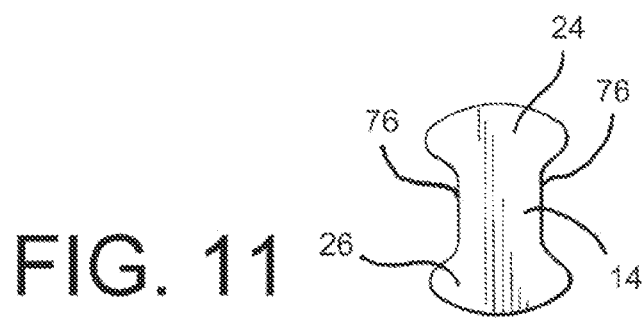
FIG. 11 shows a top elevational view of the shaft of the mandrel assembly of FIG. 10.

As best seen in FIG. 9, the opening 34 in the collar 16 feeds into a cylindrical area 44 defined by the skirt 32 of the collar. This cylindrical area 44 has a diameter greater than that of the mandrel shaft 14, and is dimensioned to receive a spring 46 (see FIG. 5) positioned around the mandrel shaft 14.

As shown in FIG. 3, a retainer or pressure washer 48 is provided to seat in the circular groove 29 of the shaft 14. The spring 46 is retained upon the shaft 14 between the retainer 48 and the circular wall 31 of the collar. As the collar 16 slides along the mandrel shaft 14, the spring biases the collar 16 away from the second end portion 22 of the shaft 14. The retainer 48 provides a stop for the collar 16, allowing the collar 16 to slide along the mandrel shaft 22 between a first position in which the shaft teeth 24 and 26 abut the head 30 of the collar 16 and a second position in which the spring 46 is compressed with the head 30 of the collar 16 forced toward the retainer 48.

With the tangs 40 and 41 of the collar teeth 36 and 38 properly positioned in the elongated grooves 28 of the shaft 14, the collar teeth 36 and 38 are offset from the shaft teeth 24 and 26. This offset allows the collar teeth 36 and 38 to mesh with the shaft teeth 24 and 26, such that the collar teeth may be moved into the same plane that contains the shaft teeth without abutment of the collar teeth and shaft teeth. This meshing action allows the collar teeth 36 and 38 to move freely in the axial direction of the shaft 14 without abutting the shaft teeth 24 and 26. Advantageously, the tangs 40 and 41 slide along the elongated grooves 28 on the mandrel shaft 14 during movement of the collar 16 in the axial direction, and thereby prevent rotation of the collar 16 with respect to the shaft 14 which would disturb the offset relationship between the collar teeth 36 and 38 and the shaft teeth 24 and 26.

An accessory 18 is configured to be attached to the mandrel assembly 12. As shown in FIG. 3, the accessory 18 is configured as a cut-off wheel 19 in one embodiment. The cut-off wheel 19 includes a disc portion 50 having an outer perimeter 52 and a central hub 54. A slot 56 is formed in the central hub 54. The slot defines a first passage 58 and an opposing second passage 59. The first passage 58 and the second passage 59 together form a bow tie shape. A support insert 60 is provided as part of the central hub 54. The support insert 60 is comprised of a strong rigid metallic material. The outer perimeter of the support insert 60 is generally ring shaped. The inner perimeter of the support insert matches the particular shape of the slot 56 of the cut-off wheel 19. In one embodiment, the support insert 60 includes an inner lip that extends into the slot 56 of the central hub 54 and provides an interior support wall for the slot 56. The cut-off wheel 19 is formed by molding the disc portion 50 from a combination of materials that include abrasive materials, resin materials, and one or more fiberglass mesh segments. Such molding process is well-known in the art of manufacturing cut-off wheels. However, typical cut-off wheels do not include support inserts such as support insert 60. Preferably, the support insert 60 is attached to the disc portion 50 by insert molding techniques. Alternatively, the support insert 60 may be secured to the disc portion 50 in any one of a number of different manners such as with adhesives or fasteners, or by friction fitting the support insert 60 within a corresponding opening defined in the disc portion 50.

Figure 4A:
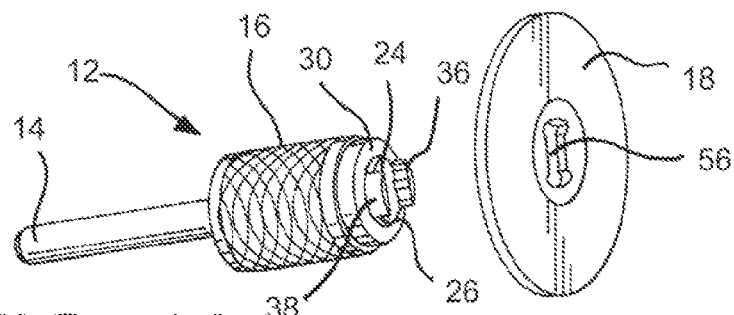
FIGS. 4A-4D show perspective views of the mandrel assembly and accessory of FIG. 1 depicting a series of steps for mounting an accessory to the mandrel assembly.

With reference now to FIGS. 4A-4D, the manner of attaching the accessory 18, such as cut-off wheel 19, to the mandrel assembly 12 is now described. In FIG. 4A, the collar 16 is in the first position with the shaft teeth 24 and 26 of the mandrel shaft 14 abutting the head 30 of the collar 16. In this position, the collar teeth 36 and 38 extend slightly past and mesh with the shaft teeth 24 and 26.

Figure 4B:
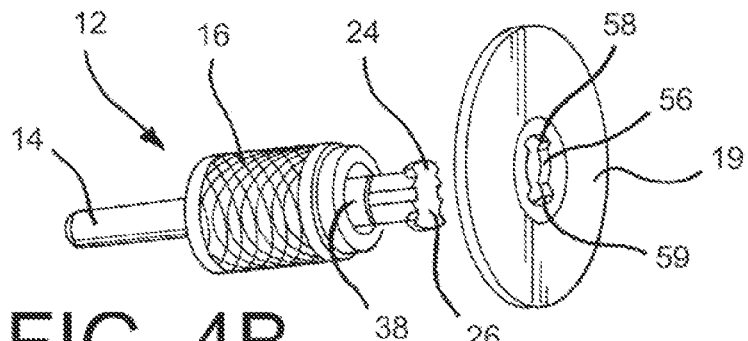

In FIG. 4B, the collar 16 is shown retracted to the second position, with the spring compressed and the shaft teeth 24 and 26 moved forward of the collar teeth 36 and 38. With the collar 16 in this second position, the slot 56 of the cut-off disc 19 is aligned with the shaft 14 such that the first shaft tooth 24 may be passed through the first passage 58 of the slot and the second shaft tooth 26 may be passed thorough the second passage 59 of the slot. The cut-off wheel 19 is then inserted over the shaft teeth 24 and 26 and onto the first end portion 21 of the shaft 14. In this position, the shaft 14 is threaded through the slot 56 of the cut-off wheel.

Figure 4C:
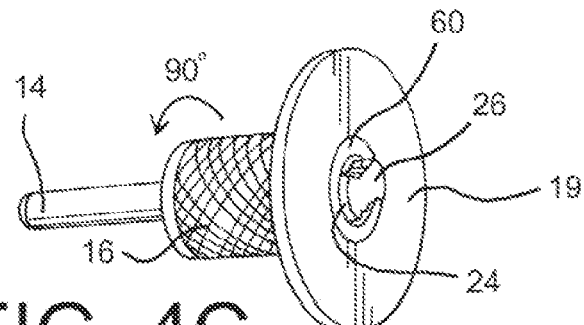
Figure 4D:
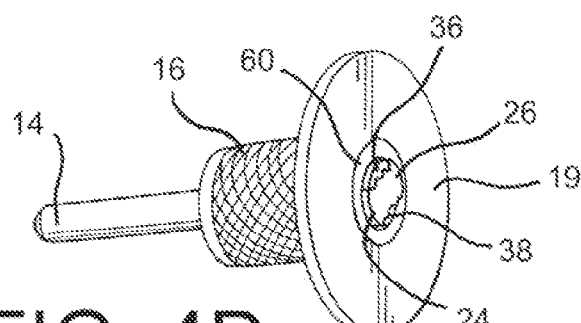

Next, with reference to FIG. 4C, the shaft 14 and collar 16 are rotated 90° relative to the cut-off disc, as noted by the arrow in FIG. 4C. With the cut-off disc in this position, the first collar tooth 36 is aligned with the first passage 58 of the slot 56 and the second collar tooth 38 is aligned with the second passage 59 of the slot. Then, as shown in FIG. 4D, the collar teeth 36 and 38 are moved through the passages 58 and 59 of the cut-off wheel slot 56, causing the collar teeth 36 and 38 to mesh with the shaft teeth 24 and 26. With the mandrel shaft 14 and collar 16 in this position, the spring 46 forces the collar 16 against the cut-off wheel 19, clamping the cut-off wheel 19 between the head 30 of the collar 16 and the shaft teeth 24 and 26. At the same time, the cut-off wheel 19 is prevented from rotating relative to the mandrel assembly 12, because the collar teeth 36 and 38 remain in the slot 56 of the cut-off wheel 19. Likewise, the collar 16 is prevented from rotating relative to the mandrel shaft 14 because the tangs 40 and 41 of the collar teeth 36 and 38 remain in the elongated grooves 28 of the mandrel shaft 14. Alternatively, instead of rotating the shaft 14 and collar 16 by 90° relative to the cut-off disc as noted by the arrow in FIG. 4C, the cut-off disc may be rotated 90° relative to the shaft 14 and the collar 16 while the shaft and collar remains stationary in order to accomplish the same relative movement between the two components.

As described above, a mandrel assembly 12 is disclosed that allows an accessory 18 to be quickly and conveniently coupled to the mandrel assembly 12 without the need for an additional tool such as a screw driver. Likewise, by reversing the above-described actions, the accessory 18 may be quickly and conveniently decoupled from the mandrel assembly 12. Therefore, a mandrel assembly is provided that may be conveniently used with numerous interchangeable accessories such as cut-off wheels, polishing wheels, grinding wheels, sanding discs, or similar articles of manufacture.

Figure 5:
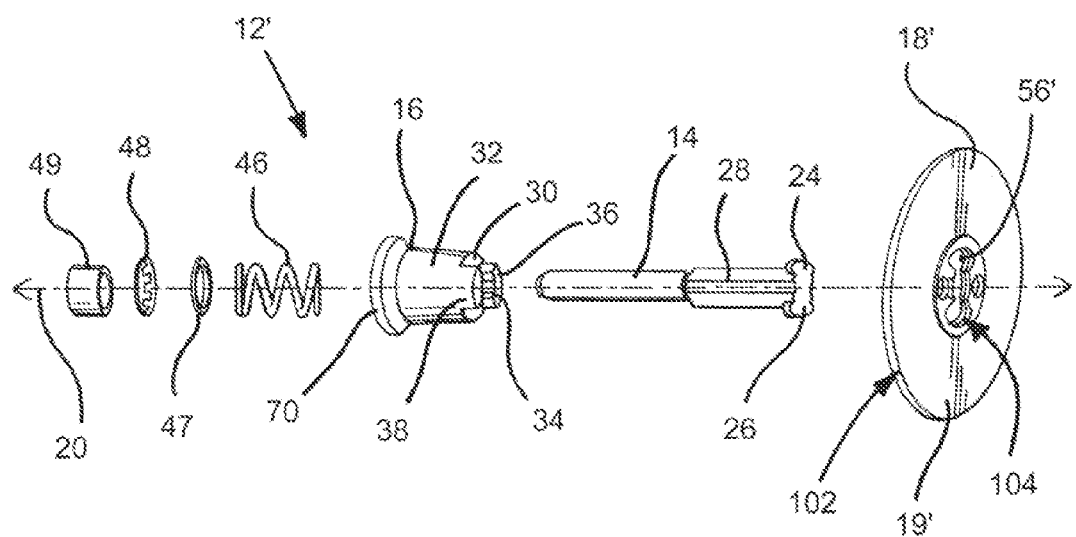
FIG. 5 shows an alternative embodiment of a mandrel assembly and an alternative accessory for use with a rotary tool.
Figure 6:
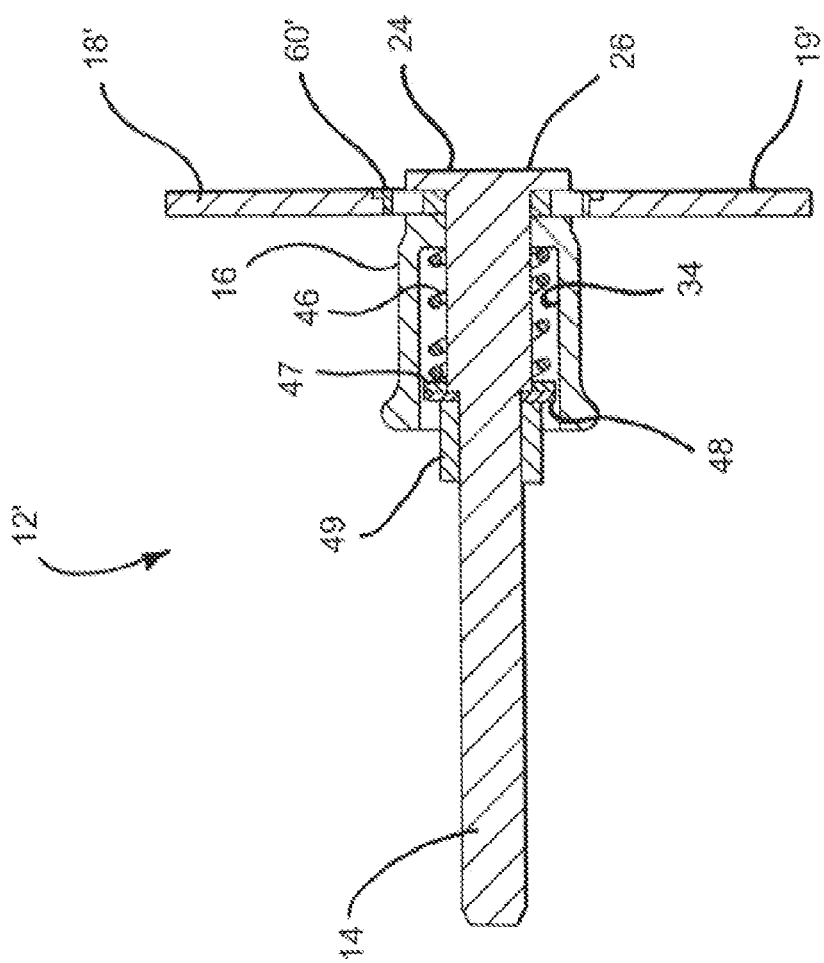
FIG. 6 shows a cross-sectional view of the mandrel assembly and accessory of FIG. 5 when the mandrel assembly is assembled and attached to an accessory.

As alluded to above, FIGS. 5-9 provide an example of an alternative embodiment of a mandrel assembly 12' that incorporates the features of the present invention therein. The mandrel assembly of this embodiment is similar to the mandrel assembly of FIGS. 1-3, but the collar 16 includes an enlarged rim 70 around the base of the skirt 32. (See FIGS. 5, 6, 9.) The enlarged rim 70 provides a gripping surface that is useful to assist a user in urging the collar 16 from the first position where the spring is less compressed (e.g., FIG. 4A) to a second position where the spring is relatively more compressed (e.g., FIG. 4B). Moreover, a ring 47 is positioned around the shaft 14 and interposed between the spring 46 and the retainer 48 as shown in FIGS. 5 and 6. In addition, a sleeve or spacer 49 is positioned around the shaft 14 and located adjacent to the retainer 48 as also shown in FIGS. 5 and 6. An accessory 18' in the form of an alternative cut-off wheel 19' (see also FIGS. 14-17) is configured to be releasably attached to the mandrel assembly 12' as shown in FIGS. 5 and 6.

The sleeve 49 functions to limit depth of insertion of the mandrel assembly 12' into a chuck of a rotary tool (not shown). In particular, when a user inserts the smaller diameter end portion of the shaft 14 into the chuck, physical interaction between the chuck and the sleeve 49 occurs thereby preventing the user from further advancing the mandrel assembly 12' into the chuck. This feature ensures that sufficient space is provided between the chuck and the open end of the collar 16 when the mandrel assembly 12' is clamped to the chuck. Leaving sufficient space between these two components ensures that the collar 16 has enough space for travel in the direction of the mandrel axis 20 (see FIG. 5) so as to allow attachment and removal of the accessory 18' to and from the mandrel assembly 12'.

Figure 12:
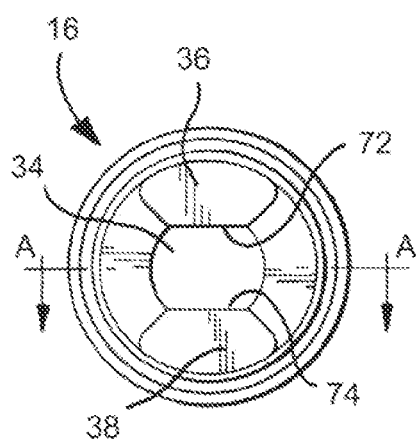
FIG. 12 shows a front elevational view of a collar of the mandrel assembly of FIG. 10.
Figure 13:
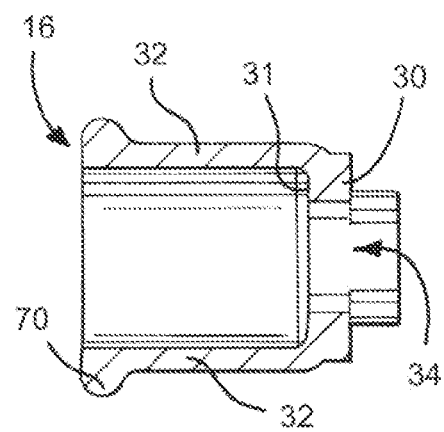
FIG. 13 shows a cross-sectional view of the collar along line A-A of FIG. 12.

FIGS. 10-13 provide an example of yet another alternative embodiment of a mandrel assembly 12" that incorporates the features of the present invention therein. As shown in FIGS. 10-13, the mandrel assembly 12" of this embodiment is similar to the mandrel assembly 12' of FIGS. 5-9, but the mandrel shaft 14 includes an elongated planar surface 76 on the first end portion of the shaft instead of an elongated groove. This elongated planar surface 76 cooperates with flat portions 72 and 74 on the collar teeth 36 and 38 as shown in FIG. 12 in order to prevent rotation of the collar 16 relative to the shaft 14. Note that the mandrel assembly 12" also includes the spring 46, the ring 47, the retainer 48, and the sleeve 49 which are positioned configured, positioned, and utilized in the same manner shown in FIGS. 5 and 6. However, for ease of understanding and clarity of description, these components have been omitted from FIG. 10. The mandrel assembly 12" is configured to be releasably attached to an accessory (not shown) that is somewhat similar to accessories 18 and 18'. One exception to such an accessory would be that the slot (somewhat similar to slot 56 of FIG. 3 and slot 56' of FIG. 10) need not have exactly the same features as slots 56, 56'. Rather, such a slot would possess a complementary configuration to the shape of the end of the shaft 14 shown in FIG. 11. However, it should be appreciated that accessories 18 and 18' would be capable of being attached to the mandrel assembly 12" even though their slots (e.g. slot 56 of FIG. 3 and slot 56' of FIG. 10) are not exactly complementary to the shape of the end of the shaft 14 shown in FIG. 11.

It should be appreciated that the mandrel assemblies 12, 12', and 12" are somewhat similar in design and thus the same reference numbers have been used to describe similar components of the assemblies for ease of understanding and clarity of description.

Figure 14:
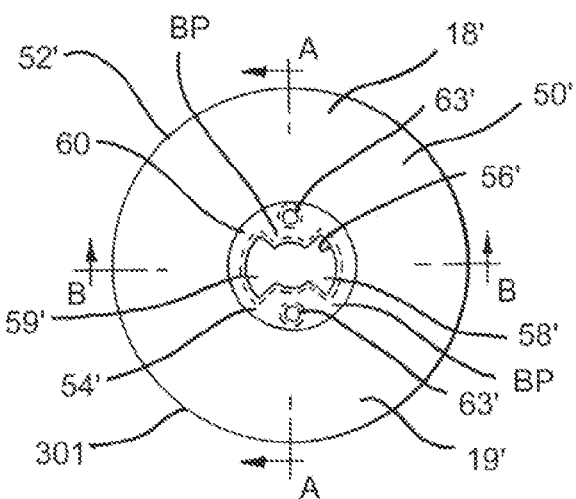
FIG. 14 is an elevational view of the accessory of FIG. 5.
Figure 15:
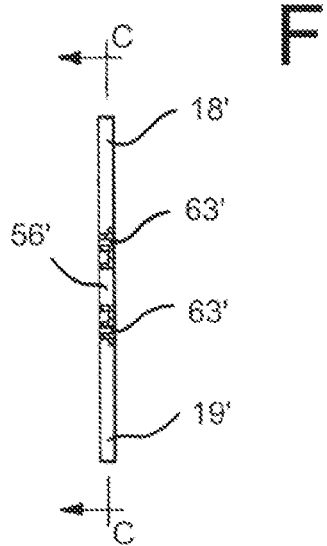
FIG. 15 shows a cross-sectional view of the accessory along line A-A of FIG. 14.
Figure 16:
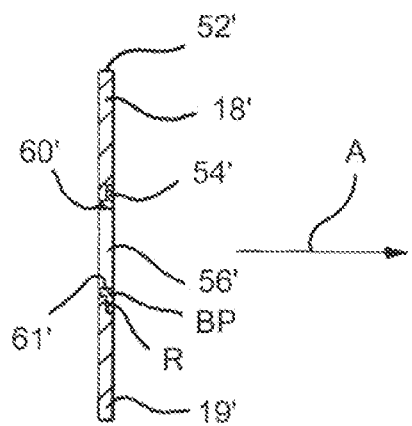
FIG. 16 shows a cross-sectional view of the accessory along line B-B of FIG. 14.
Figure 17:
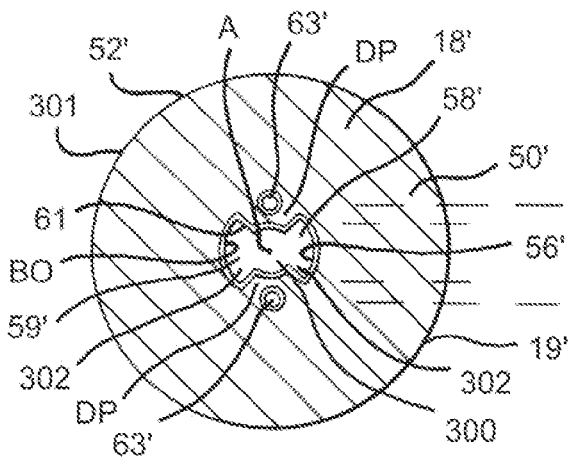
FIG. 17 shows a cross-sectional view of the accessory along line C-C of FIG. 15.

Turning now to FIGS. 14-18, the cut-off wheel 19' is described in more detail. The accessory 18' is made from the same materials and in the same manner as that described hereinabove with regard to the accessory 18. The cut-off wheel 19' includes a disc portion 50' having an outer perimeter 52' and a central hub 54'. A slot 56' is formed in the central hub 54'. The slot defines a first passage 58' and an opposing second passage 59'. The first passage 58' and the second passage 59' together form a bow tie shape. A support insert 60' is provided as part of the central hub 54'. The support insert 60' is comprised of a strong rigid metallic material, and is secured to the disc portion 50' of the cut-off wheel 19'. The outer perimeter of the support insert 60' is generally ring shaped. The inner perimeter of the support insert matches the particular shape of the slot 56' of the cut-off wheel 19'. The support insert 60' includes an inner lip 61' that extends into the slot 56' of the central hub 54' and provides an interior support wall for the slot 56'. The support insert 60' further includes two downwardly extending cylinder portions 63' as shown in FIGS. 14, 15, and 17. Alternatively, FIGS. 18A, 18B 18C, 18D and 18E show another support insert 60" that has identical construction and function as the support insert 60' with a couple of exceptions. The first exception is that the support insert 60" includes a number of anti-rotation spikes 300 that extend downwardly from a bottom surface 301 of the support insert 60" as shown in FIGS. 18A, 18B 18C, 18D and 18E. The spikes 300 function to further inhibit relative rotation of the support insert 60" in relation to the disc portion 50'. The second exception is that instead of having two cylinder portions 63' that extend downwardly as shown in FIGS. 14, 15, and 17, the support insert 60" includes two circular openings 63" as shown in FIGS. 18A, 18B 18C, 18D and 18E. The two circular openings 63" are created by a lancing or drilling operation that includes advancing a tool bit into a top surface of the support insert 60" and out through a bottom surface of the support insert 60". Such an operation causes a certain amount of displaced material to extend downwardly from the bottom surface 301 around the periphery of each circular opening 63". This certain amount of displaced material functions, as the anti-rotation spikes 300 do, to further inhibit relative rotation of the support insert 60" in relation to the disc portion 50'.

Figure 18:
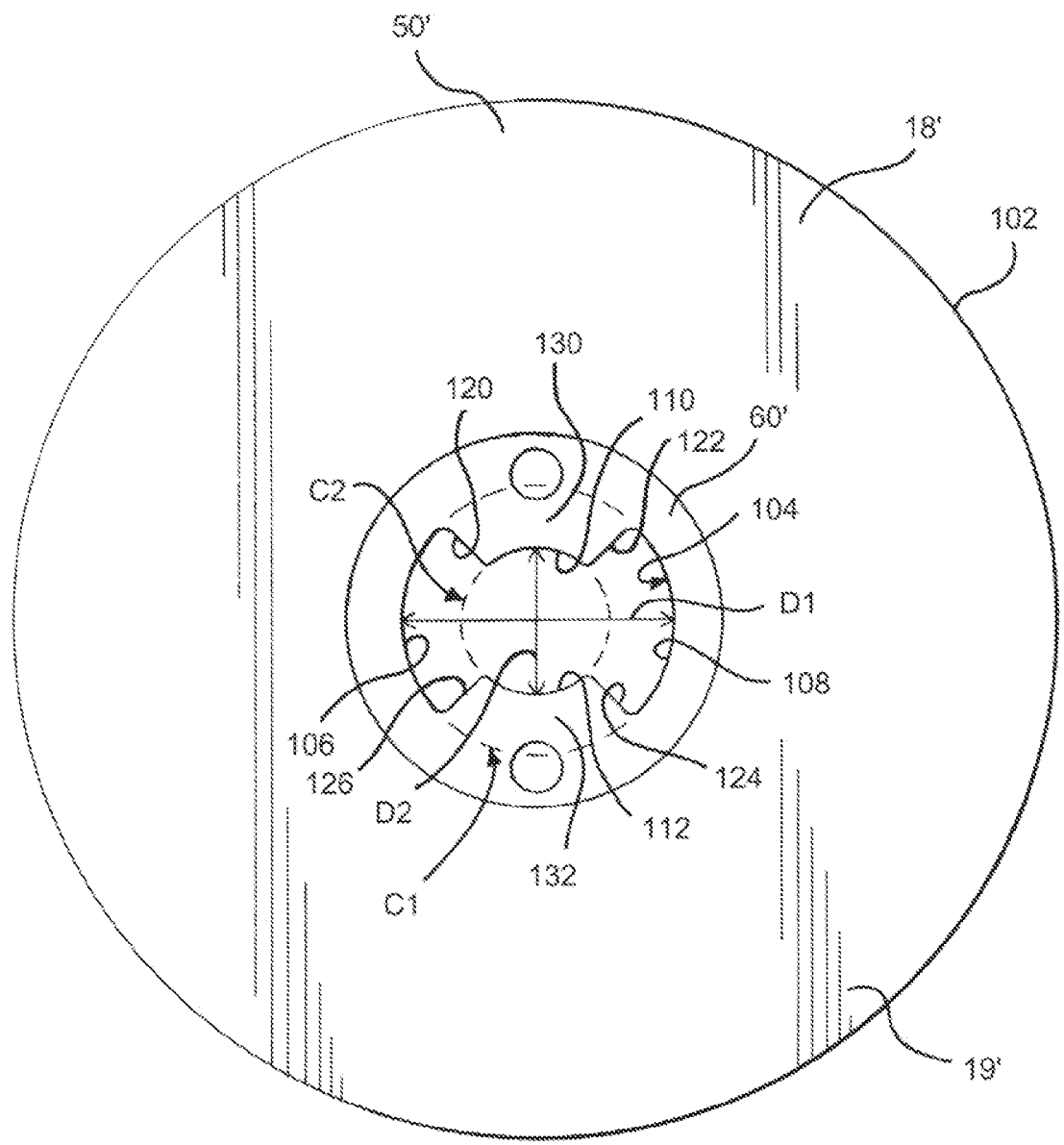
FIG. 18 shows an enlarged front elevational view of the accessory shown in FIG. 5.
Figure 18A:
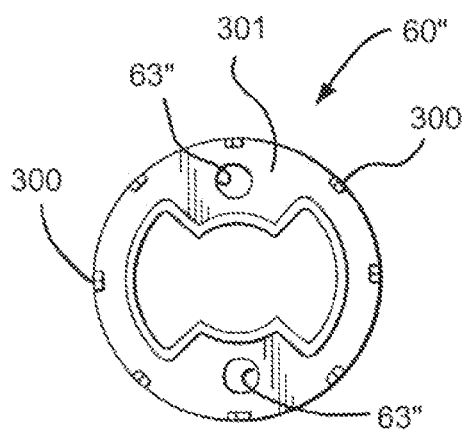
FIGS. 18A, 18B, 18C, 18D, and 18E show various views of an alternative embodiment of a support insert that may be used in place of the support insert of the accessory shown in FIGS. 14-18.
Figure 18B:
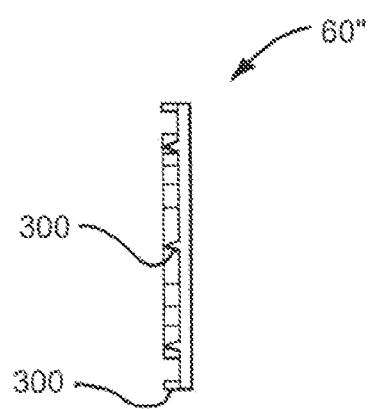
Figure 18C:
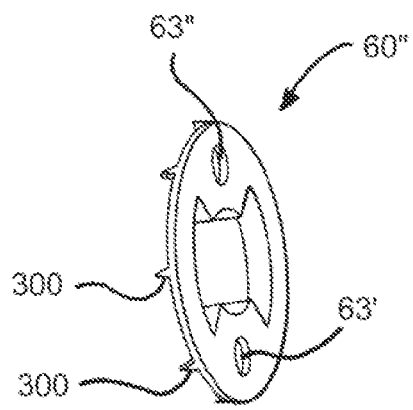
Figure 18D:
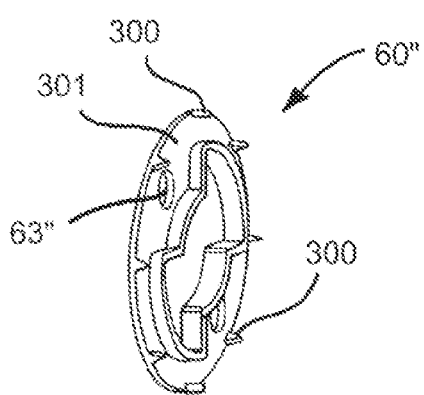
Figure 18E:
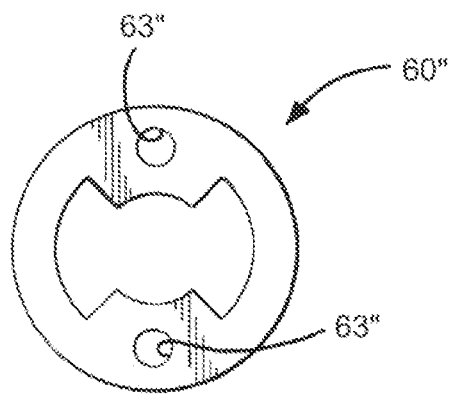

As shown in FIG. 18, the accessory 18' includes an outer wall structure 102 that defines a circular outer periphery. The accessory 18' further includes an inner wall structure 104 that defines a coupling opening. The inner wall structure 104 includes a first inner wall portion 106, a second inner wall portion 108, a third inner wall portion 110, and a fourth inner wall portion 112. The first inner wall portion 106 defines an arc of a first circle C1 having a first diameter D1. The second inner wall portion 108 defines another arc of the first circle C1 having the first diameter D1. The third inner wall portion 110 defines an arc of a second circle C2 having a second diameter D2. The fourth inner wall portion 112 defines another arc of the second circle C2 having the second diameter D2. The first diameter D1 is greater than the second diameter D2. Each of the first arc and the second arc extends for a distance that is greater than forty-five (45) degrees in relation to the first circle C1. Preferably, each of the first arc and the second arc extends for a distance that is approximately equal to ninety (90) degrees in relation to the first circle C1.

The inner wall structure 104 further includes (i) a planar fifth inner wall portion 120 connecting the first inner wall portion 106 to the third inner wall portion 110, (ii) a planar sixth inner wall portion 122 connecting the third inner wall portion 110 to the second inner wall portion 108, (iii) a planar seventh inner wall portion 124 connecting the second inner wall portion 108 to the fourth inner wall portion 112, and (iv) a planar eighth inner wall portion 126 connecting the first inner wall portion 106 to the fourth inner wall portion 112.

The accessory 18' further includes a first clamping flange 130 that is offset from the first inner wall portion 106 and the second inner wall portion 108. The first clamping flange 130 includes the third inner wall portion 110 as shown in FIG. 18. Also, the accessory 18' additionally includes a second clamping flange 132 that is offset from the first inner wall portion 106 and the second inner wall portion 108. The second clamping flange 132 includes the fourth inner wall portion 112 as also shown in FIG. 18.

Figure 19:
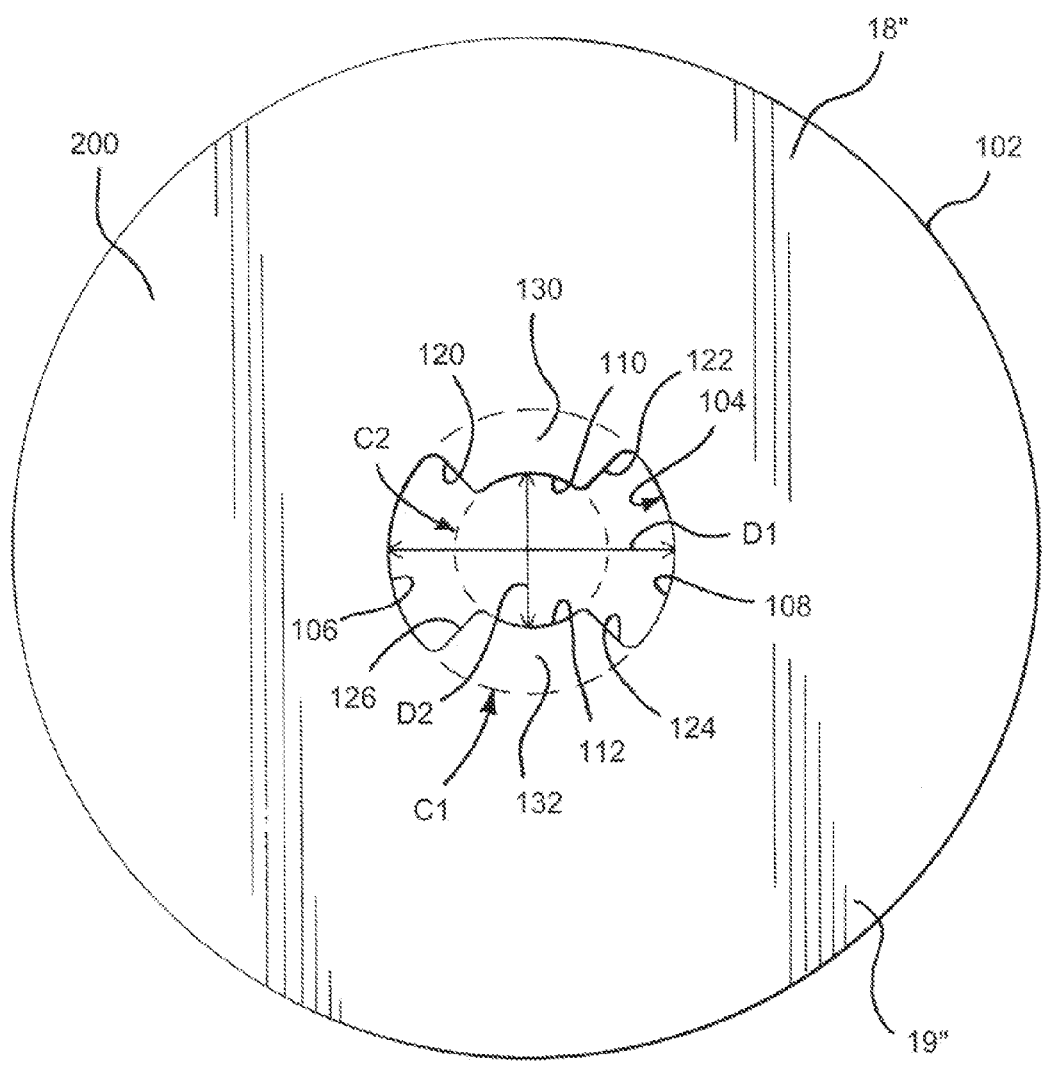
FIG. 19 shows another embodiment of an accessory that may be used with the mandrel assemblies of FIGS. 1, 5, and 10.

FIG. 19 shows another alternative embodiment of an accessory 18" that may be used with any of the mandrel assemblies 12, 12', and 12" described herein, and in the same manner described herein as the accessory 18' is described herein as being used with any of mandrel assemblies 12, 12', and 12". Since the accessory 18" is somewhat similar in design to the accessory 18' described above, the same reference numbers have been used to describe similar components of the assemblies for ease of understanding and clarity of description. The difference between the accessory 18' and the accessory 18" is that the accessory 18" does not include an insert. Rather, the accessory 18" includes a body 200 that includes the outer wall structure 102 and the inner wall structure 104. The body 200 is made from the same materials and in the same manner as that described hereinabove with regard to the disc portion 50 of the accessory 18.

Figure 20:
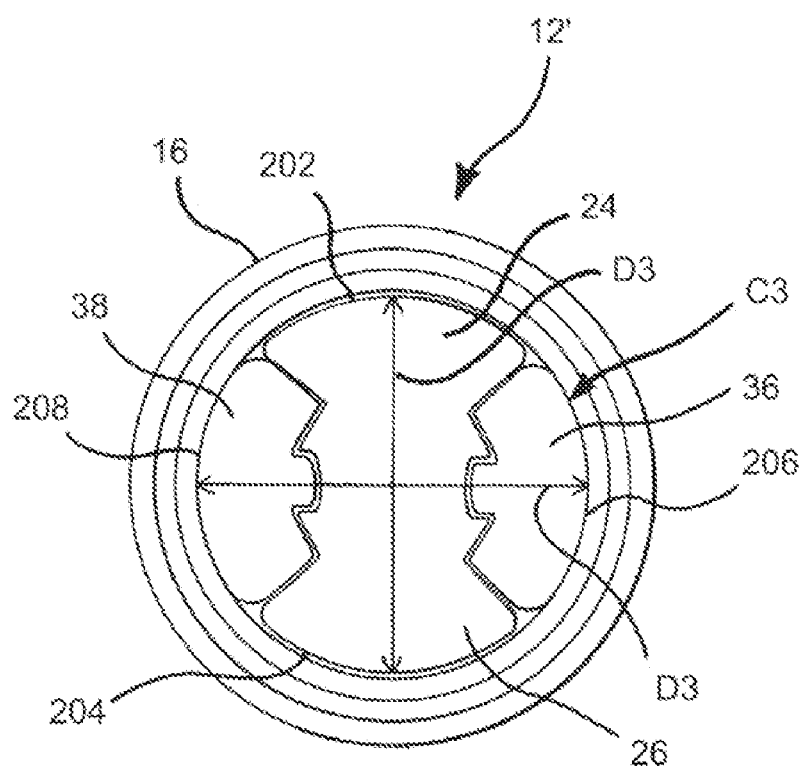
FIG. 20 shows a front elevational view of the mandrel assembly of FIG. 5 in an assembled state.

Turning now to FIG. 20, there is shown a front elevational view of the mandrel assembly 12' in an assembled state. The first shaft tooth 24 includes a first outer shaft tooth wall portion 202 defining an arc of a third circle C3 having a third diameter D3. The second shaft tooth 26 includes a second outer shaft tooth wall portion 204 defining an arc of the third circle C3 having the third diameter D3. The first collar tooth 36 includes a first outer collar tooth wall portion 206 defining an arc of the third circle C3 having the third diameter D3. And the second collar tooth 38 includes a second outer collar tooth wall portion 208 defining an arc of the third circle C3 having the third diameter D3. It should be appreciated that the third diameter D3 is greater than the second diameter D2 (see FIGS. 18 and 19), but less than the first diameter D1 (see FIGS. 18 and 19). The allows the accessory 18, 18' and 18" to be secured to and firmly held by the mandrel assembly 12, 12', and 12". Also, each of the arcs defined by the first outer shaft tooth wall portion 202, the second outer shaft tooth wall portion 204, the first outer collar tooth wall portion 206, and the second outer collar tooth wall portion 208 extends for a distance that is greater than forty-five (45) degrees in relation to the third circle C3. Preferably, each of the arcs defined by the first outer shaft tooth wall portion 202, the second outer shaft tooth wall portion 204, the first outer collar tooth wall portion 206, and the second outer collar tooth wall portion 208 extends for a distance that is approximately equal to ninety (90) degrees in relation to the third circle C3.

Figure 17A:
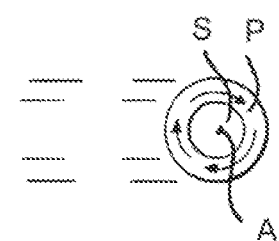
FIG. 17A depicts (i) the space S that contains the first opening portion 300 during rotation of the body of the accessory of FIG. 17 about the axis A, and (ii) the path P that both the drive portions DP and the second opening portions 302 travel during rotation of the body of the accessory of FIG. 17 about the axis A.

As can be seen in FIGS. 14-18, the accessory 18' includes a body that defines an axis of rotation A and has a work piece contacting surface 301 and two drive portions DP. The body has defined therein a body opening BO including a first opening portion 300 and two second opening portions 302. The accessory 18' further includes the support insert 60' located within the body opening BO. The first opening portion 300 is contained within a space S depicted in FIG. 17A during rotation of the body about the axis A. Both the drive portions DP and the second opening portions 302 are advanced through a path P depicted in FIG. 17A during rotation of the body about the axis A. As depicted in FIG. 17A, the path is located outside of the space S. Note that the body of the accessory 18' defines a recess R that surrounds the body opening BO, and a base portion BP of the support insert 60' extends from the inner lip 61' of the support insert 60'.

Although the present invention has been described with respect to certain preferred embodiments, it will be appreciated by those of skill in the art that other implementations and adaptations are possible. For example, differently shaped teeth may be provided on the shaft and the collar which are different from the teeth described herein. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A rotary tool accessory, comprising:
    a body defining an axis of rotation and having a work piece contacting surface and a drive portion, said body having defined therein a body opening including a first opening portion and a second opening portion; and
    an insert located within at least said second opening portion,
    wherein said first opening portion is contained within a space during rotation of said body about said axis,
    wherein both said drive portion and said second opening portion are advanced through a path during rotation of said body about said axis, said path being located outside of said space,
    wherein said body includes an inner wall structure that defines said body opening, wherein said insert includes (i) a lip portion positioned within said body opening and adjacent to said inner wall structure, and (ii) a base portion connected to said lip portion and extending away from said body opening, wherein said body further defines a recess that surrounds said body opening, and wherein said base portion is positioned within said recess.

2. The rotary tool accessory of claim 1, wherein said insert is located in both said first opening portion and said second opening portion.

3. The rotary tool accessory of claim 1, wherein:
said body further includes an outer wall structure defining a circular outer periphery, and
said work piece contacting surface is located at said circular outer periphery.

4. The rotary tool accessory of claim 3, wherein:
said body includes a fiberglass mesh material, and
said insert is made of a metallic material.

5. The rotary tool of claim 1, wherein:
said body includes a first surface and an opposite second surface,
said recess is defined in said first surface, and
said lip portion includes an end that terminates at said opposite second surface.

6. The rotary tool of claim 1, wherein:
said insert further includes a plurality of anti-rotation spikes extending from said base portion,
each of said plurality of anti-rotation spikes are spaced apart from said lip portion, and
each of said plurality of anti-rotation spikes extend in the same direction as the lip portion.

7. A rotary tool accessory, comprising:
a body defining an axis of rotation and having a work piece contacting surface and a drive portion, said body having defined therein a body opening positioned adjacent to said drive portion; and
an insert attached to said body,
wherein said body opening includes a first opening portion and a second opening portion,
wherein said first opening portion is contained within a space defined by a circle during rotation of said body about said axis,
wherein said drive portion is advanced through a path during rotation of said body about said axis, said oath being located outside of said circle,
wherein said second opening portion is advanced through said path during rotation of said body about said axis,
wherein at least part of said insert is positioned within said second opening portion,
wherein said body includes an inner wall structure that defines said body opening,
wherein said insert includes (i) a lip portion positioned within said body opening and adjacent to said inner wall structure, and (ii) a base portion connected to said lip portion and extending away from said body opening,
wherein said body further defines a recess that surrounds said body opening, and
wherein said base portion is positioned within said recess.

8. The rotary tool accessory of claim 7, wherein said insert is located in both said first opening portion and said second opening portion.

9. The rotary tool accessory of claim 7, wherein:
said body further includes an outer wall structure defining a circular outer periphery, and
said work piece contacting surface is located at said circular outer periphery.

10. The rotary tool accessory of claim 7, wherein:
said body includes a fiberglass mesh material, and
said insert is made of a metallic material.

11. The rotary tool of claim 7, wherein:
said body includes a first surface and an opposite second surface,
said recess defined in said first surface, and
said lip portion includes an end that terminates at said opposite second surface.

12. The rotary tool of claim 7, wherein:
said insert further includes a plurality of anti-rotation spikes extending from said base portion,
each of said plurality of anti-rotation spikes are spaced apart from said lip portion, and
each of said plurality of anti-rotation spikes extend in the same direction as the lip portion.

13. A rotary tool accessory, comprising:
a body having (i) an outer wall structure defining a circular outer periphery, (ii) an inner wall structure defining a body opening, and (iii) a drive portion that defines a portion of said inner wall structure; and
an insert located within said body opening,
wherein said body opening includes a first opening portion and a second opening portion,
wherein said first opening portion is contained within a space during rotation of said body about said axis,
wherein said drive portion is advanced through a path during rotation of said body about said axis, said path being located outside of said space,
wherein said second opening portion is advanced through at least part of said path during rotation of said body about said axis,
wherein at least part of said insert is positioned within said second opening portion,
wherein said insert includes (i) a lip portion positioned within said body opening and in contact with said inner wall structure, and (ii) a base portion connected to said base portion and extending away from said body opening,
wherein said body further defines a recess that surrounds said body opening, and
wherein said base portion is positioned within said recess.

14. The rotary tool accessory of claim 13, wherein said insert is located in both said first opening portion and said second opening portion.

15. The rotary tool accessory of claim 13, wherein said body further includes a work piece contacting portion located at said circular outer periphery.

16. The rotary tool accessory of claim 13, wherein:
said body includes a fiberglass mesh material, and
said insert is made of a metallic material.

17. The rotary tool of claim 13, wherein:
said body includes a first surface and an opposite second surface,
said recess is defined in said first surface, and
said lip portion includes an end that terminates at said opposite second surface.

18. The rotary tool of claim 13, wherein:
said insert further includes a plurality of anti-rotation spikes extending from said base portion,
each of said plurality of anti-rotation spikes are spaced apart from said lip portion, and
each of said plurality of anti-rotation spikes extend in the same direction as the lip portion.

* * * * *